(12) United States Patent
Haglund et al.

(10) Patent No.: US 7,261,007 B2
(45) Date of Patent: Aug. 28, 2007

(54) CIRCUMFERENTIAL SLOT VIRTUAL IMPACTOR FOR CONCENTRATING AEROSOLS

(75) Inventors: John S. Haglund, College Station, TX (US); Andrew R. McFarland, Houston, TX (US)

(73) Assignee: The Texas A&M University System, College Station, TX (US)

( * ) Notice: Subject to any disclaimer, the term of this patent is extended or adjusted under 35 U.S.C. 154(b) by 389 days.

(21) Appl. No.: 10/995,745

(22) Filed: Nov. 22, 2004

(65) Prior Publication Data

US 2006/0054017 A1 Mar. 16, 2006

Related U.S. Application Data

(60) Provisional application No. 60/524,204, filed on Nov. 21, 2003.

(51) Int. Cl.
*G01N 1/40* (2006.01)
*B01D 45/04* (2006.01)

(52) U.S. Cl. .............. 73/863.21; 73/28.04; 55/452; 95/32

(58) Field of Classification Search .................. 73/863.21–863.22, 28.04–28; 95/32–33; 55/452
See application file for complete search history.

(56) References Cited

U.S. PATENT DOCUMENTS

| | | | |
|---|---|---|---|
| 4,301,002 A | 11/1981 | Loo | |
| 4,972,957 A | 11/1990 | Liu et al. | |
| 5,425,802 A | 6/1995 | Burton et al. | |
| 5,571,945 A | 11/1996 | Koutrakis et al. | |
| 5,788,741 A | 8/1998 | Burton et al. | |
| 5,858,043 A * | 1/1999 | Geise | 95/32 X |
| 5,932,795 A | 8/1999 | Koutrakis et al. | |
| 5,999,250 A * | 12/1999 | Hairston et al. | 356/73 |
| 6,010,554 A * | 1/2000 | Birmingham et al. | 95/32 |
| 6,386,015 B1* | 5/2002 | Rader et al. | 73/31.05 |

(Continued)

FOREIGN PATENT DOCUMENTS

CH 604843 A * 9/1978 .................. 55/452

(Continued)

OTHER PUBLICATIONS

Haglund et al., A Circumferential Slot Virtual Impactor, *American Association for Aerosol Research*, Apr. 27, 2004, pp. 664-674.

*Primary Examiner*—Thomas P. Noland
(74) *Attorney, Agent, or Firm*—Patterson, Thuente, Skaar & Christensen, P.A.

(57) ABSTRACT

A circumferential slot virtual impactor includes a disk-shaped housing with an endless circumferential slot for receiving aerosols. The slot forms an acceleration nozzle, and a receiver nozzle spaced apart radially inwardly from the acceleration nozzle exit. In an annular gap between the two nozzles, negative pressure is selectively applied to draw a major flow of the aerosol axially away from the nozzles, while a minor flow of the aerosol is drawn radially inward and enters the receiver nozzle. A portion of the larger particles leaves the major flow and merges with the minor flow due to particle momentum, thus increasing the large-particle concentration of the minor flow. The acceleration nozzle incorporates convex curvature along its opposed interior surfaces, for a smoother aerosol flow and reduced large-particle deposition.

38 Claims, 12 Drawing Sheets

U.S. PATENT DOCUMENTS

| | | |
|---|---|---|
| 6,402,817 B1 | 6/2002 | Bergman |
| 6,664,550 B2 * | 12/2003 | Rader et al. .............. 250/461.2 |
| 7,034,549 B2 * | 4/2006 | Richardson et al. ........ 324/636 |
| 7,178,380 B2 * | 2/2007 | Shekarriz et al. .......... 73/28.04 |
| 2001/0032519 A1 | 10/2001 | Liu et al. |
| 2002/0124664 A1 * | 9/2002 | Call et al. ................ 73/863.22 |
| 2002/0157993 A1 * | 10/2002 | Call et al. .................... 209/143 |
| 2006/0096393 A1 * | 5/2006 | Pesiri ...................... 73/863.21 |

FOREIGN PATENT DOCUMENTS

| | | | |
|---|---|---|---|
| DE | 195 04 275 A1 | 8/1996 | |
| JP | 02017921 A * | 1/1990 | .................... 95/32 |

* cited by examiner

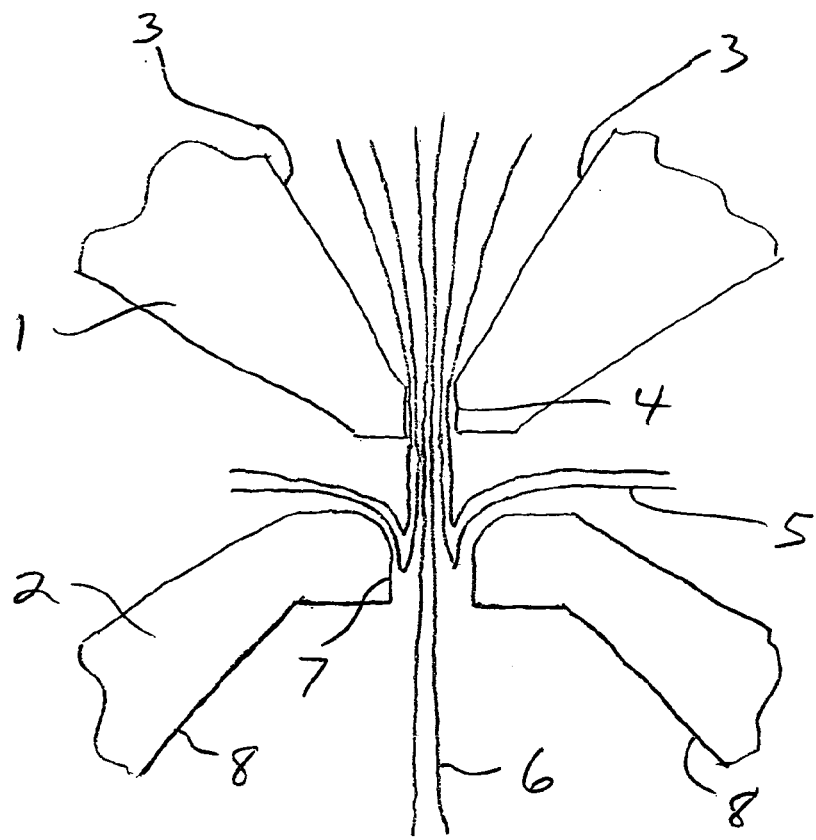
FIG. 1
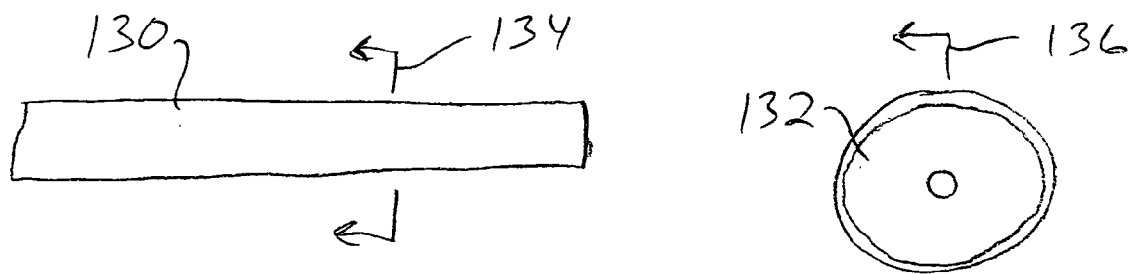
FIG. 14  FIG. 15

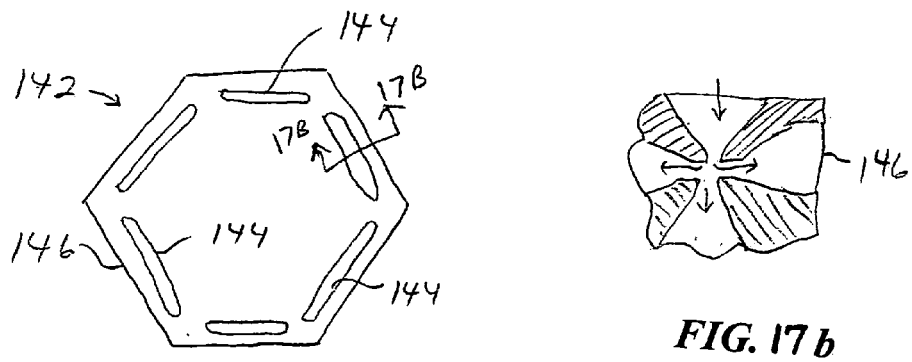
FIG. 17a
FIG. 17b
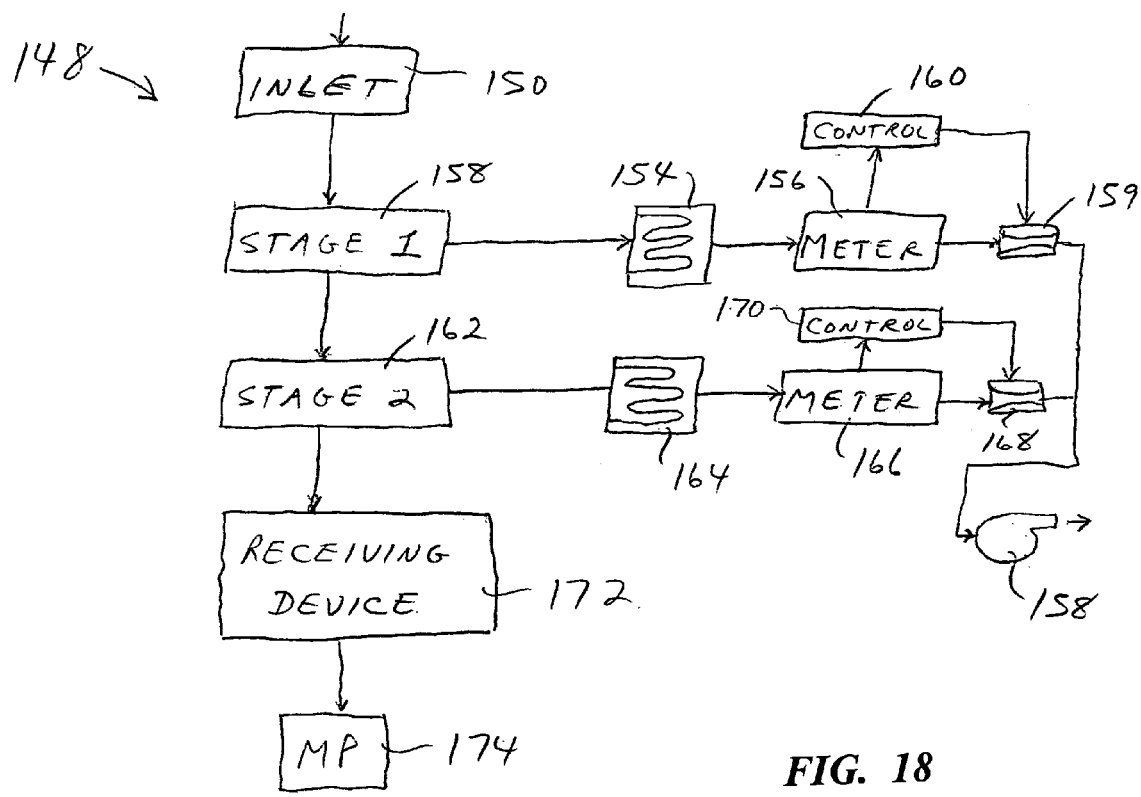
FIG. 18

CIRCUMFERENTIAL SLOT VIRTUAL IMPACTOR FOR CONCENTRATING AEROSOLS

This application claims the benefit of priority based on Provisional Application No. 60/524,204 entitled "Circumferential Slot Virtual Impactor for Concentrating Aerosols," filed Nov. 21, 2003, which Application is incorporated by reference herein.

The United States government has rights in this invention pursuant to Contract No. DAAH04-96-C-0086 between U.S. Army Soldier Biological and Chemical Command (SBCCOM), Aberdeen Proving Ground, Maryland through Battelle Research Triangle Park, North Carolina, and the Texas Engineering Experiment Station (TEES), and Contract No. DAAD13-02-C-0064 between SBCCOM and TEES.

BACKGROUND OF THE INVENTION

Systems for detecting potentially hazardous airborne particulate matter in near-real-time can be used in military and civilian applications for nuclear, biological and chemical aerosols. In the nuclear industry, radioactive particulate continuous air monitors protect personnel in laboratories and industrial facilities. The U.S. military has field-deployable chemical and biological (CB) agent-detection systems to protect personnel in the event of a CB attack. Anthrax attacks experienced by the U.S. Postal Service in 2001 and the sarin nerve-agent attack in the Tokyo subway system in 1995 indicate a need for CB detectors in sensitive civilian locations. Although chemical agent and radioactive particulate detectors have matured through several design generations, practical biological point detection systems are relatively new, and significant advancements are needed before biological agent detectors perform on par with chemical agent and radioactive particulate monitors.

A major obstacle confronting biological detectors is the relatively low concentration of biological agent particles that can cause serious harm. In terms of the minimum detectable level in the sampled environment and reliability of the detector output signal, detector response can be enhanced by concentrating the sampled aerosol particles prior to detection. Concentration factors of 100 to 1000 are currently employed in detection systems. Sensitivity in future biological detection systems is likely to improve, which could potentially reduce the desired levels. Nonetheless, even future detection systems will benefit from aerosol concentration prior to detection, in that the greater number of organisms detected, the higher the probability of a statistically supportable alarm. For current and future applications, there is a critical need for small, portable, biological agent detection systems that are suitable for field applications and can efficiently concentrate airborne particles.

Virtual impaction is widely used for concentrating aerosol particles. The most common configurations in present virtual impactors are axi-symmetric, in which opposed acceleration and receiver nozzles are truncated-conical or round, and planar-symmetric in which the nozzles have opposed, inclined rectangular surfaces spaced apart to form slots with rectangular exits. The concept of virtual impaction can be understood from FIG. 1, which schematically illustrates an aerosol flow through an acceleration nozzle 1 and a receiver nozzle 2 of a virtual impactor. The aerosol (including particles suspended in a gaseous medium or gas phase) is drawn into accelerator nozzle 1 by a partial vacuum (negative pressure differential), and is accelerated by virtue of inclined surfaces 3 of nozzle 1 as it approaches an aperture 4. The aerosol flows longitudinally (vertically in the figure) through aperture 4 and into a fractionation zone in the gap between nozzles 1 and 2. As the aerosol flow enters the fractionation zone, negative or vacuum pressure is selectively applied to draw a major portion or fraction of the aerosol (in terms of volume per unit time) transversely away from the fractionation zone. The major flow, illustrated by streamlines 5, approaches nozzle 2 but undergoes a hairpin turn, doubles back toward nozzle 1, then flows into a diverging transverse exit passage. The gaseous medium and the smaller entrained particles tend to follow the path indicated by streamlines 5. In contrast, the larger particles tend to continue moving longitudinally into receiver nozzle 2, because they have momentum sufficient to overcome the tendency to flow with the gaseous medium.

Negative pressure also is applied through nozzle 2 to draw a minor portion or fraction of the aerosol flow longitudinally into the receiver nozzle. The minor flow, indicated by streamlines 6, passes through an aperture 7 into nozzle 2. Inclined nozzle surfaces 8 diverge to decelerate the flow. The gaseous medium and all particles of the minor portion tend to follow the longitudinal path indicated by streamlines 8.

Typically, the major flow constitutes about ninety percent of the original flow in terms of volume per unit time, while the minor flow constitutes about ten percent of the original flow. With the exception of losses due to deposition onto the walls near the fractionation zone, virtually all of the larger particles are transferred from the major flow to the minor flow, to provide a highly concentrated minor flow including about ten percent of the gaseous medium, ten percent of the smaller particles, and nearly all of the larger particles.

The larger particles and smaller particles are distinguished from one another based on a size threshold known as the cutpoint, i.e. the size at which particle momentum causes fifty percent of the particles to leave the major flow and merge into the minor flow. As particle sizes increase above the cutpoint, the percentage of the particles transferred from the major flow to the minor flow increases rapidly. Consequently, in polydisperse aerosols, virtually all of the larger particles are transferred to the minor flow, although very large particles may inadvertently be deposited on internal surfaces in the fractionation zone and thereby not transferred to the minor flow stream.

Aerosol (particle and gas phase) flow in a virtual impactor is governed primarily by two dimensionless parameters, the Stokes number (Stk) and the Reynolds number (Re). The Stokes number is given by:

$$Stk = \frac{C_c \rho_p D_p^2 U_0}{18 \mu L_c} \quad (1)$$

where $D_p$ is the particle diameter in centimeters, $\rho_p$ is the particle density in kg/m$^3$, $C_c$ is the slip correction factor, $U_0$ is the mean velocity at the expiration nozzle exit in m/second, $L_c$ is the acceleration nozzle aperture dimension (radius of a circular nozzle aperture and half-width of a slot nozzle) in m, and $\mu$ is the dynamic viscosity of the gas in kg/m s.

The Reynolds number is given by:

$$Re = \frac{\rho_f L_c U_o}{\mu} \quad (2)$$

where $\rho_f$ is the gas density in kg/m$^3$, and the other values are as indicated above, except that the characteristic dimension $L_c$ is the nozzle diameter for a circular nozzle and the nozzle width for a rectangular slot nozzle.

The Stokes number is the dominant parameter governing particle behavior in virtual impactors. The cutpoint Stokes number (Stk$_{50}$) corresponding to the cutpoint particle size is weakly a function of the Reynolds number owing to minor differences in the flow field as affected by Reynolds number.

The pressure drop ($\Delta P$) for moving air through the virtual impactor can be represented as a function of the acceleration nozzle throat velocity:

$$\Delta P = K \frac{\rho_f U_o^2}{2} \quad (3)$$

where: K is a pressure coefficient, essentially constant for a limited range of flow rates.

The ideal power (Pwr) required to operate a virtual impactor, i.e. the minimum power required to move air through the virtual impactor ignoring blower/pump inefficiencies and pressure losses in the associated flow handling system, is given by:

$$\text{Pwr} = Q_{ma}\Delta P_{ma} + Q_{mi}\Delta P_{mi} \quad (4)$$

where: $Q_{ma}$ is the major flow rate (of the fine particle flow in cm/sec); $\Delta P_{ma}$ is the difference between pressure at the entrance plane of the acceleration nozzle and pressure at the exhaust plane of the major flow in pascals (Pa); $Q_{mi}$ is the minor (coarse particle) flow rate in cm/sec; and $\Delta P_{mi}$ is the difference between pressure at the entrance plane of the acceleration nozzle and pressure at the exhaust plane of the minor flow in Pa. Typically, the major flow components on the right side of Equation 4 are much larger than the minor flow components, because $Q_{ma}$ is much larger than $Q_{mi}$ (e.g. by a factor of nine). Also, the pressure drop for the minor flow is negligible compared to the pressure drop for the major flow because of pressure recovery in the entry region of the receiver nozzle.

For bioaerosol concentration, the virtual impactor should have a cutpoint below the particle size range of interest. A bacterial agent like anthrax may consist of single-spores having aerodynamic diameters of about 0.9 µm. To achieve a cutpoint low enough to concentrate particles of this size with an acceptable level of power consumption, the virtual impactor must have the proper nozzle dimension (width or diameter) and mean nozzle velocity. For a given cutpoint the choices are (i) a larger nozzle dimension and higher mean nozzle velocity, and (ii) a smaller nozzle dimension and a lower mean nozzle velocity.

With a fixed cutpoint and flow rate, the ideal power to operate a virtual impactor is a function of nozzle width, increasing approximately with the square of the nozzle diameter or width (for a constant minor loss coefficient K). FIG. 2 is a plot of ideal power for operating a virtual impactor with a cutpoint aerodynamic diameter of 0.8 microns at a flowrate at 500 L/min (17.7 CFM), with a pressure coefficient K of 1.5. An impactor with a smaller nozzle dimension requires less power for a given cutpoint and flowrate. For example, a slit width of 0.254 mm (0.010 inches) requires an ideal power of 40 watts, while an impactor with a slit width of 0.762 mm (0.030 inches) requires 400 watts.

Present bioaerosol detection systems typically require flow rates in the range of 100 to 1000 L/min to reliably detect concentrations of biological agents expected in a release. For small dimension round-nozzle virtual impactors, these flow rates require an array of many nozzles. For slot nozzles, the total slot length must be sufficient to supply the required total flow, either as one continuous slot, or as an array of slots of intermediate length. Both approaches involve manufacturing difficulties, especially as the nozzle critical dimension approaches the level of tolerance control.

An array of many round nozzles increases the risk of producing defective nozzles, in that each nozzle requires small dimension chamfers and fillets. For slot nozzles, nozzle edge linearity and parallelism become more difficult to achieve as the nozzle dimension becomes smaller. Both designs require precise alignment mechanisms to align the centers of the receiver nozzle and acceleration nozzle. Also, both require considerable depth for the acceleration and receiver nozzles to gradually accelerate the aerosol particles approaching the fractionation zone and decelerate the large particles after fractionation. Thus, manufacturing processes such as photo-etching are of limited value.

As compared to round nozzles, slot nozzles are more resistant to fouling from debris. Round nozzles are more easily bridged by airborne fibers. Once a fiber bridges the nozzle, additional particles attach to the fiber, eventually fouling the nozzle and preventing proper function of the virtual impactor. Although slot nozzles can also become bridged by fibers, their long dimension allows them to avoid fouling to a greater degree. On the other hand, round nozzles are not subject to the inaccuracies introduced by disturbances at the opposite ends of the rectangular slots, known as end effects.

Neither the round nozzle design nor the rectangular-slot nozzle design is particularly well suited for a portable, compact aerosol particle concentration device with a minimal power requirement. In the case of round nozzles, this is due to the requirement for an array of nozzles to meet flow rate requirements. In the case of rectangular-slot nozzles, it is due either to the array requirement, or an inordinate length necessary to achieve a desired flow rate. Further, the nozzle interior in both designs leads to undesirable large-particle trajectory effects as the aerosol moves through the acceleration nozzle. More particularly and with reference to FIG. 1, large particles relatively close to one side of the nozzle can tend to travel transversely toward the opposite side of the aperture rather than flowing longitudinally through the aperture with the gaseous medium, due to particle momentum.

Therefore, it is an object of the present invention to provide an aerosol particle concentrating device that operates effectively at both micrometer and sub micrometer cutpoints, yet is compact and has low power requirements.

Another object is to provide a virtual impactor having an acceleration nozzle with a high ratio of slot length to slot width, which is not subject to end effects.

A further object is to provide an improved process for separating an aerosol into fractions with different particulate concentrations.

Yet another object is to provide a virtual impactor that promotes a more unidirectional flow of particles through the aperture of its acceleration nozzle.

SUMMARY OF THE INVENTION

To achieve these and other objects, there is provided a particle concentrating device for separating a primary aerosol flow into secondary and tertiary aerosol flows with different particle concentrations. The device includes a housing having a perimeter wall. The housing includes a housing structure defining a first fluid passage running lengthwise along the perimeter wall, open to an exterior of the housing, and extending inward from the housing wall to a first-passage exit to accommodate a primary flow of an aerosol in an inward first direction with respect to the housing. The aerosol comprises a gaseous medium and particles suspended in the medium. The particles comprise first particles having aerodynamic diameters above a selected threshold, and second particles having aerodynamic diameters below the selected threshold. The housing structure further defines a second fluid passage downstream of the first fluid passage, to accommodate fluid flow away from the first-passage exit in a second direction different from the first direction. The housing structure further defines a third fluid passage disposed inwardly of the first fluid passage, to accommodate fluid flow away from the first-passage exit in the first direction. A first fluid-drawing component, in fluid communication with the second fluid passage, is adapted to draw a first portion of the primary flow toward and into the second fluid passage and thereby deflect the gaseous medium and second particles of the first portion, while the first particles of the first portion tend to continue moving in the first direction due to particle momentum. This provides a secondary flow of the aerosol through the second fluid passage. A second fluid-drawing component, in fluid communication with the third passage, is adapted to draw a second portion of the primary flow inward toward and into the third fluid passage. This provides a tertiary flow of the aerosol through the third fluid passage. The tertiary flow comprises the gaseous medium and particles of the second portion merged with first particles of the first portion.

In a preferred embodiment, the housing is generally disk shaped. The perimeter wall is a circumferential wall having a circular profile, the first direction is radially inward, and the second direction is axial with respect to the housing. This provides a housing that is compact, yet provides a favorably high ratio of slot length to slot width. For example, a disk shaped housing with a diameter of 127 mm (5 inches) would have a circumferential slot length of about 400 mm which, when used with a slot width of 0.5 mm would yield a length/width ratio of 800. A linear (rectangular slot) virtual impactor with the same slot width would need to be 40 cm in length.

An added advantage of the circumferential slot, as compared to the linear or rectangular-slot devices, is that the circumferential slot is annular and therefore endless. Undesirable end effects are eliminated.

To achieve the desired ratio of flow rates of the secondary and tertiary flows, known as the major and minor flows based on their comparative volumetric flow rates, valves are coupled between the second fluid passage and a vacuum pump, and between the third fluid passage and the pump. The valves are governed by controllers to maintain the desired flow rates. Typically, the major flow rate is about 90 percent of the primary flow rate, and the minor flow rate is about 10 percent of the primary flow rate. In effect, the large-particle concentration of the tertiary flow is greater than the same concentration in the primary flow by a factor of ten.

To further concentrate the aerosol particles, several of the concentrated devices can be operated in series, with the tertiary flow output from a first device being provided as an input aerosol to a second, substantially identical aerosol particle concentrating device. In a fractionating zone of the second device, the tertiary flow is divided into separate parts, one of which is deflected (except for the larger particles) while the other part is drawn further inward. Assuming the same 90/10 ratio of the major flow to the minor flow, the minor flow output of the second device has a large-particle concentration of about 100 times that of the original aerosol.

Another aspect of the invention is a process for separating an aerosol into fractions with different particulate concentrations, including:

a. causing an aerosol to enter an enclosure through an entrance along a perimeter wall of the enclosure and to flow inside the enclosure in a first direction toward an interior region of the enclosure, wherein the aerosol comprises a gaseous medium and particles suspended in the medium, and the particles comprise first particles having aerodynamic diameters above a selected threshold and second particles having aerodynamic diameters below the selected threshold;

b. at a fractionation region in the enclosure, causing the gaseous medium and second particles of a first portion of the aerosol to flow in a second direction different from the first direction while the first particles of said first portion continue to move in the first direction due to particle momentum, thus to provide a first fractional flow of the aerosol including the gaseous medium and second particles of said first portion;

c. simultaneously at the fractionation region, causing a second portion of the aerosol to continue flowing in the first direction, thus to provide a second fractional flow of the aerosol comprising the gaseous medium and particles of said second portion in combination with the first particles of said first portion.

As a further step, the aerosol of the second fractional flow can be characterized in a variety of ways, including counting the particles, collecting the particles for later analysis, and detecting biological particles. For example, the second fractional flow of the aerosol can be provided to an instrument designed to irradiate the particles with short wavelength radiation (e.g. ultraviolet radiation) and sense fluorescence emitted by particles in response to the irradiation. One such instrument is described in U.S. Pat. No. 5,999,250. In this fashion, ambient aerosols with particle concentrations too low for effective real-time detection can be provided to the detector at considerably enhanced levels of concentration to promote more reliable detection.

Another aspect of the invention is an aerosol particle concentrating device. The device includes an acceleration nozzle including a nozzle entrance, a nozzle exit including an exit aperture, and a nozzle wall having an interior surface running from the nozzle entrance to the nozzle exit. The interior surface defines a first fluid passage for accommodating an aerosol flow through the acceleration nozzle in a first longitudinal direction from the entrance to the exit. The exit aperture has a major transverse dimension and a minor transverse dimension. The device includes structure defining a second fluid passage downstream of the first fluid passage to accommodate fluid flow away from the nozzle exit in a second direction different from the first longitudinal direction, and a third fluid passage longitudinally downstream from the first fluid passage to accommodate fluid flow away from the nozzle exit in the first longitudinal direction. A fluid-drawing component, in communication with the second and third fluid passages, draws first and second fractions of the aerosol flow into and through the second and third fluid passages respectively. At least some of the particles of the first fraction separate from the first fraction and enter the third fluid passage with the second fraction due to particle momentum. The interior surface, at least in and along longitudinal planes taken through the acceleration nozzle in the direction of the minor transverse dimension, forms pairs of opposed surface profiles substantially symmetrical about a longitudinal axis through the acceleration nozzle. The profiles incorporate respective arcuate segments between the entrance and the exit aperture. Each arcuate segment is convex in a direction toward the longitudinal axis. The opposed arcuate segments converge in said first longitudinal direction to diminish the transverse distance between the opposed surface profiles.

The arcuate surface profile segments promote a smoother, more unidirectional flow of the aerosol as it travels through the acceleration nozzle and undergoes acceleration. In conventional nozzle designs, the opposed inside surface profiles are linear, typically at an angle of 30-40 degrees from the longitudinal axis. The profile segments along the exit aperture are parallel to the axis. As a result of this profile, the aerosol near the interior walls is traveling at the 30-40 degree angle relative to the longitudinal direction. The general aerosol flow becomes more longitudinal as it enters the exit aperture. However, some of the larger particles, due to their momentum, continue to travel at an angle relative to the longitudinal direction, thus traveling toward the opposite side of the exit aperture, to the point of deposition onto an opposite interior surface.

The arcuate surface profiles provided in accordance the present invention form the desired convergence to accelerate the aerosol flow, yet also minimize cross-over trajectories. As a result, particle losses through deposition are reduced, the aerosol flows more smoothly through the particle concentration device, and measurements based on the concentration device output are more reliable.

IN THE DRAWINGS

For a further appreciation of the above and other features and advantages, reference is made to the following detailed description and to the drawings, in which:

FIG. 1 is a schematic view illustrating the concept of virtual impaction;

FIG. 14 is an illustration of a linear slot virtual impactor constructed in accordance with the present invention;

FIG. 15 illustrates an axi-symmetric particle concentrating device constructed according to the present invention;

FIGS. 17A and 17B are frontal and sectional views of another alternative embodiment aerosol particle concentration device; and FIG. 18 is a diagrammatic view of an aerosol characterizing system employing two particle concentrating stages in accordance with the present invention.

DETAILED DESCRIPTION OF THE PREFERRED EMBODIMENTS

Figure 2:
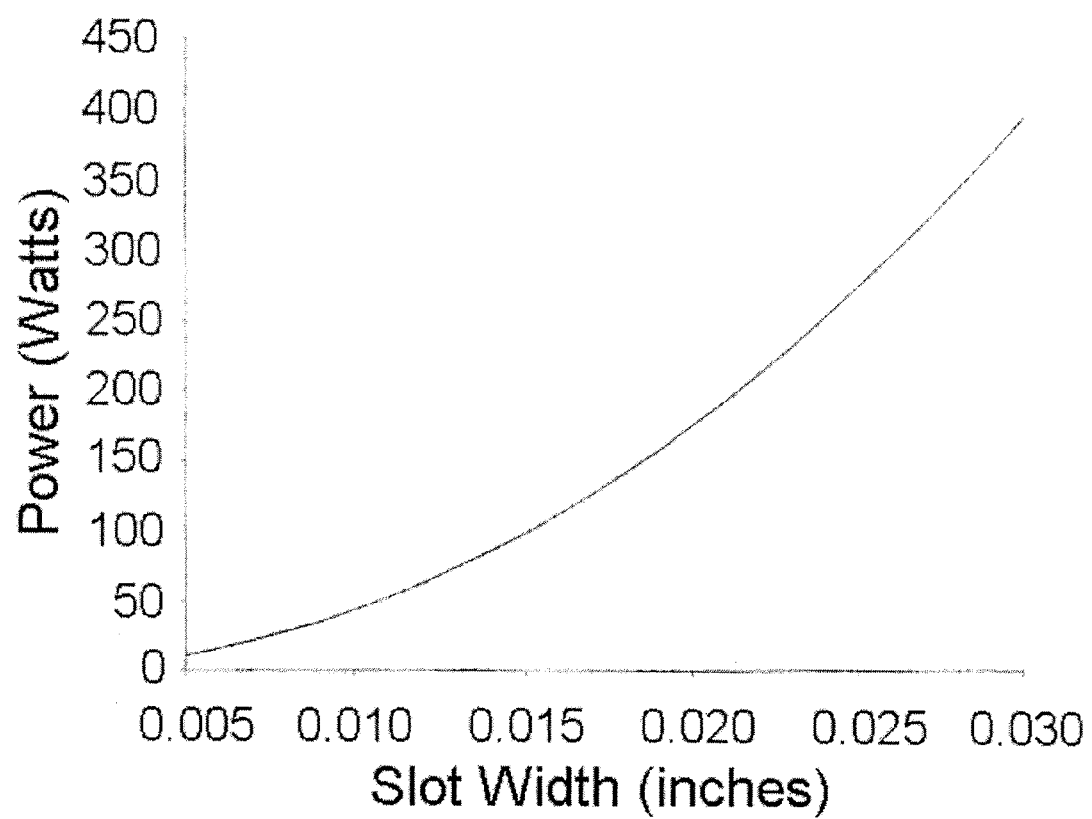
FIG. 2 is a plot of ideal power to operate a virtual impactor as a function of slot width.
Figure 4:
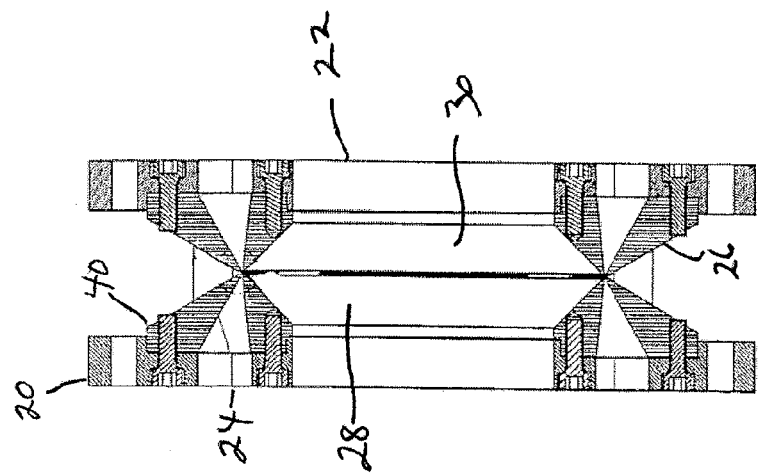
FIG. 4 is a sectional view taken along the line 4-4 in FIG. 3.
Figure 3:
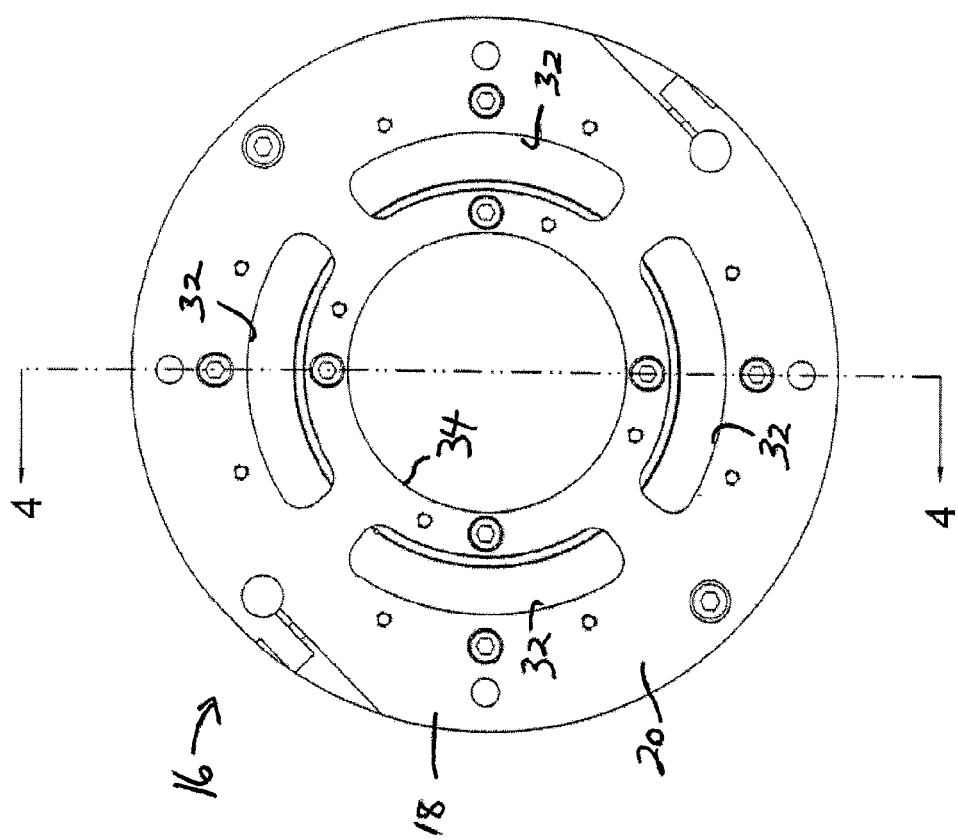
FIG. 3 is a frontal view of an aerosol particle concentrating device constructed in accordance with the present invention.
Figure 5:
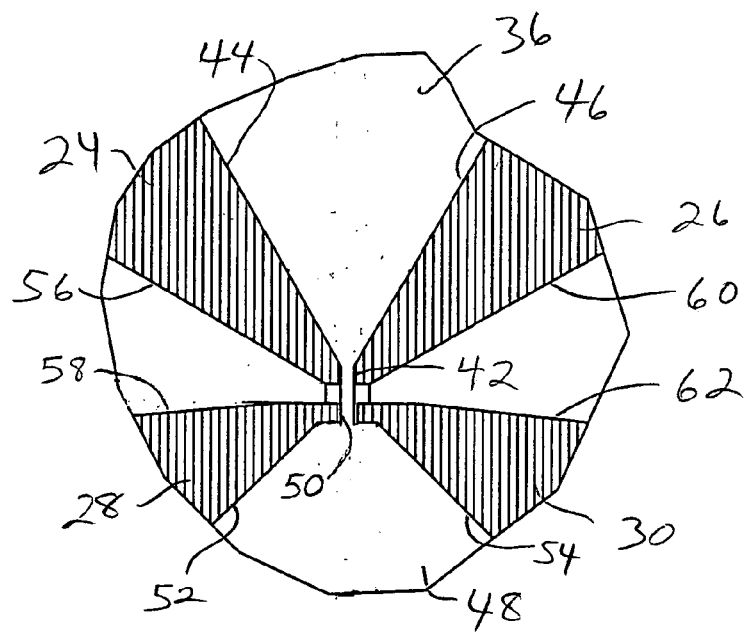
FIG. 5 is an enlarged view showing part of FIG. 4.

Turning now to the drawings, there is shown in FIGS. 3 and 4 an aerosol particle concentrating device 16 including a disk shaped housing 18 formed of several annular components. As best seen in FIG. 2, the annular components include a frontal housing section 20 and a rearward housing section 22. Additional annular components that cooperate to form fluid flow directing nozzles, include a frontal outer nozzle section 24, a rearward outer nozzle section 26, a frontal inner nozzle section 28 and a rearward inner nozzle section 30. Bolts 32 are used to couple the annular components together and maintain them in coaxial alignment.

A plurality of arcuate openings 32 are formed through the frontal wall portion of housing section 20. Rearward housing section 22 includes similar arcuate openings. Also formed through housing section 20 is a circular central opening 34.

Nozzle sections 24 and 26 cooperate to form an annular acceleration nozzle 36 adapted to receive an aerosol and guide the aerosol into housing 18 while accelerating the aerosol. The aerosol is drawn radially inward from a nozzle entrance 40 toward a nozzle exit aperture 42 having opposed annular radial surfaces. Opposed interior surfaces 44 and 46 of nozzle 36 are inclined at an angle of about 30 degrees from the radial direction, to provide a convergence to accelerate the incoming aerosol.

Nozzle sections 28 and 30 cooperate to provide an annular receiver nozzle 48, aligned with and radially spaced apart from acceleration nozzle 36. Sections 28 and 30 are spaced apart transversely, i.e. axially with respect to the housing, to form a receiver nozzle aperture 50 having opposed annular surfaces. Opposed annular inclined surfaces 52 and 54 provide a divergence in the radially inward direction, to decelerate aerosols moving through the nozzle.

Between nozzles 36 and 48, the nozzle sections have respective annular inclined surfaces 56, 58, 60, and 62. Opposed annular surfaces 56 and 58, and opposed surfaces 60 and 62, cooperate to provide diverging passages in opposite directions, axial with respect to housing 18 and perpendicular to the radial direction of aerosol flow through nozzle aperture 42.

A fluid-drawing system including a vacuum pump and several valves, not shown in FIGS. 1-3, is used to apply a partial vacuum to receiver nozzle 48 and to the gap between nozzles 36 and 48 As noted above in connection with FIG. 1, this creates a fractionation zone between the nozzles. In the fractionation zone, the incoming or primary aerosol flow is divided into a secondary flow that travels axially away between surfaces 56 and 58 (and also between surfaces 60 and 62), and a tertiary flow that enters receiver nozzle 48. Also as noted in connection with FIG. 1, the negative pressures are selectively adjusted to provide the secondary flow as a major flow constituting about 90 percent of the primary aerosol flow in terms of volume per unit time, while the tertiary flow constitutes a minor flow at about 10 percent of the primary flow. The separation of larger particles from the secondary flow, and their merger into the tertiary flow to provide a highly concentrated aerosol, occur as explained in connection with FIG. 1.

Given the shape of housing 18, the interior of acceleration nozzle 36 forms an endless annular or circumferential slot for receiving the aerosol. In fact, device 16 can be conveniently thought of as a circumferential slot virtual impactor. The design is particularly well suited for uses that demand portability, compactness, and low power consumption. As previously noted, power consumption can be reduced by narrowing the slot width, i.e. the axial width of exit aperture 42. This requires considerable slot length, e.g. one hundred times the slot width, to achieve satisfactory volumetric flow rates. In the circumferential slot design, the slot "length" is substantially equal to the circumference of the housing. A conventional linear slot virtual impactor, to achieve the same flow rate through the same slot width, would need to be over three times as long as the diameter of housing 18.

An additional advantage with respect to linear slot designs is that the annular slot eliminates the undesirable end effects that negatively influence the performance of linear devices.

The circumferential slot nozzle performs in the same manner as linear slot designs, provided that the total slot length and critical geometries are equivalent, and that the radius of curvature of the slot is much greater than the slot width. Short linear slot impactors may experience increased particle losses due to end effects, which are absent in systems with circumferential slots. In an exemplary circumferential virtual slot device, the diameter of the circumferential slot is 70 mm (2.75"), for a total slot length of 219 mm (8.64 inches). The acceleration nozzle slot width is 0.51 mm (0.020 inches), providing a ratio of the radius of slot curvature to slot width of approximately 69. A sampling flow rate with a low pressure drop requires a long slot. For the exemplary device, the ratio of slot length to slot width is 432.

Figure 6:
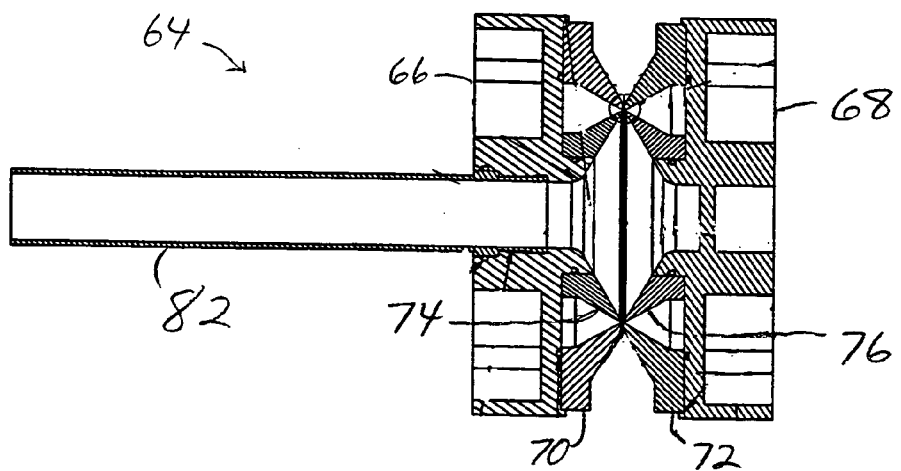
FIG. 6 is a sectional view of an alternative embodiment aerosol particle concentration device.

FIG. 6 is a sectional view of an alternative embodiment aerosol particle concentration device 64. Annular housing sections 66 and 68 cooperate with annular nozzle sections 70, 72, 74, and 76 as before to provide an annular acceleration nozzle 78, an exit aperture 79, a receiver nozzle 80, and diverging passages between the two nozzles. A conduit 82, attached to the housing at the center of housing section 66, conducts the tertiary aerosol flow away from the device.

Figure 7:
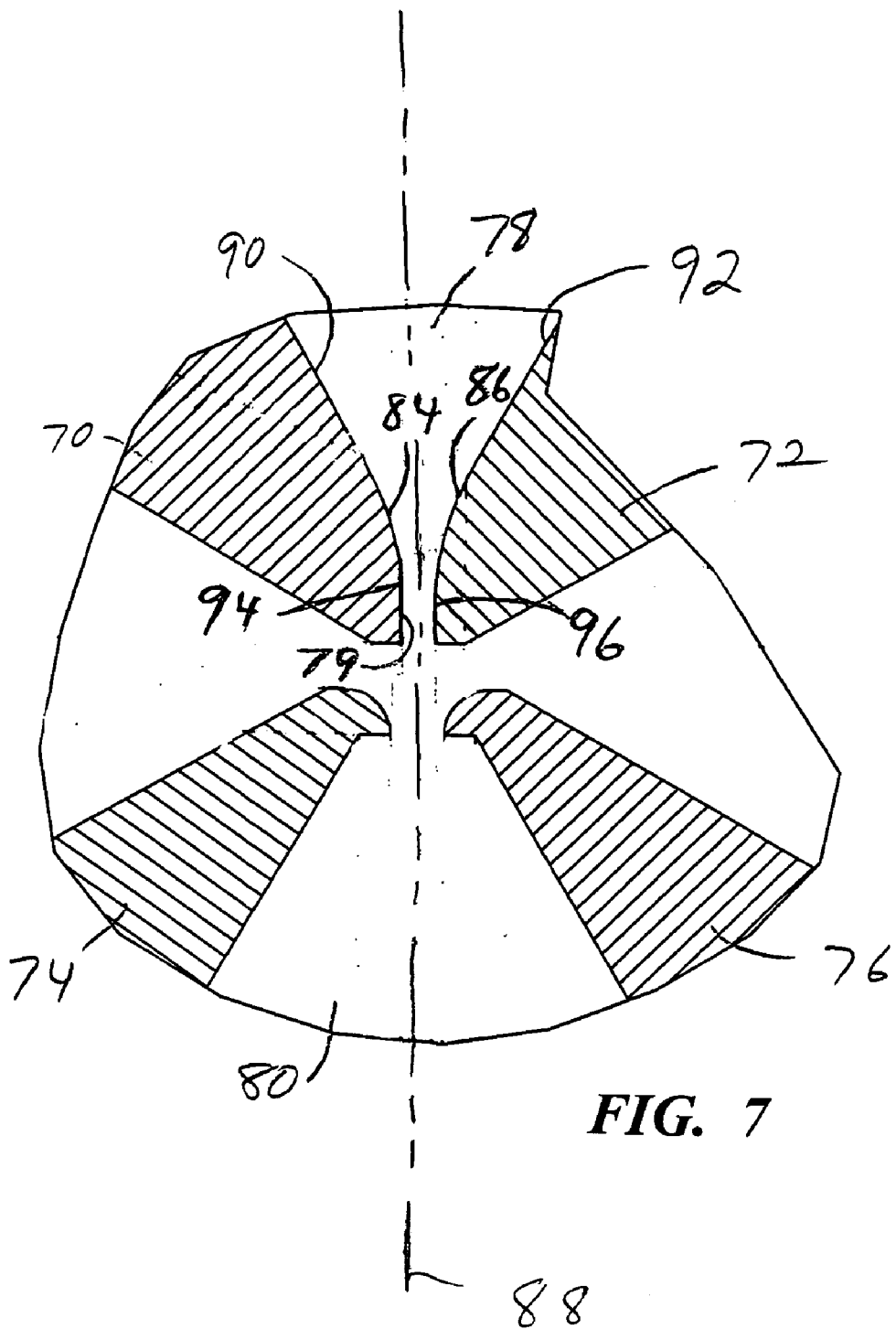
FIG. 7 is an enlarged view showing part of FIG. 6.

With reference to FIG. 7, the nozzle sections are selectively curved to provide flow-smoothing features. Nozzle sections 70 and 72, forming opposed interior surfaces of acceleration nozzle 78, incorporate respective arcuate segments 84 and 86. The arcuate segments are on opposite sides of a central plane that appears in FIG. 7 as a longitudinal (vertical) axis 88. Each arcuate segment is convex in the direction toward the center plane, and has a radius of curvature in the range of five times to fifteen times the transverse width of aperture 79. More preferably, the radius of curvature is about ten times the width. Thus, the interior surfaces of nozzle 78 incorporate a gradual, smooth curve between opposed nozzle surface segments 90 and 92 inclined relative to the center plane, and segments 94 and 96 of exit aperture 79 that are parallel to the center plane. Segments 94 and 96 form tangents to arcuate segments 84 and 86.

Although nozzles with linear inclined surface segments that taper to vertical exit-aperture segments can satisfactorily accelerate incoming aerosols, the curvature shown in FIG. 7 affords several advantages. First, the curvature provides for a smoother flow of the entire aerosol. This curvature also considerably reduces losses from large-particle crossover. In planar-surface designs, portions of the incoming aerosol flow along the opposed inclined surfaces, and thus carry particles at an angle relative to the longitudinal center plane. As the aerosol enters the exit aperture, the gaseous component and smaller particles are channeled into a longitudinal flow direction. Larger particles tend to continue moving at an angle relative to the longitudinal center plane, crossing the exit aperture transversely, and in some cases becoming deposited onto the surface of the aperture. The nozzle surface curvature, by providing a more gradual transition in flow direction, counteracts this tendency.

Figure 8:
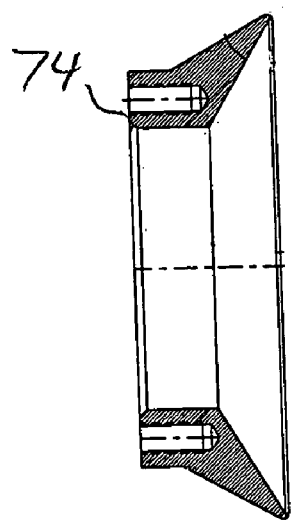
FIGS. 8 and 9 are sectional views of annular nozzle sections forming parts of the device shown in FIG. 6.
Figure 9:
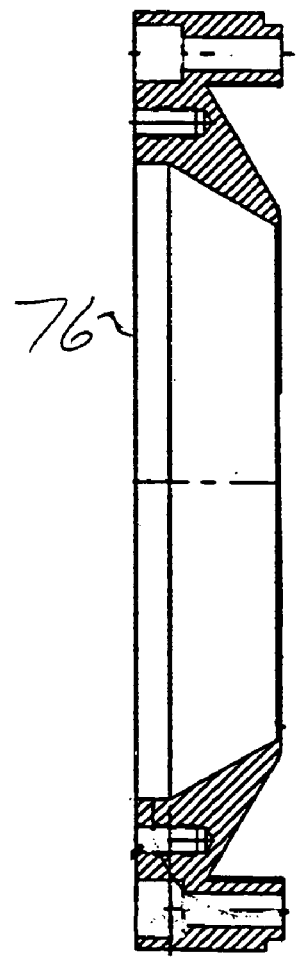

FIGS. 8 and 9 illustrate, respectively, inner frontal nozzle section 74 and outer frontal nozzle section 70 of concentrating device 64. The counterpart rear nozzle sections are substantially the same.

The circumferential slot devices disclosed herein are preferably formed by fabricating pairs of the nozzle sections or blades to form the two halves of each nozzle, and joining them with bolts to form the nozzle. The blades are fabricated with conventional precision lathes, with electrical discharge machining (EDM), or combinations of the two. Those skilled in the art will recognize that fabrication can also involve machining a single piece of material through a combination of conventional and advanced machining techniques, such as EDM. The devices also can be fabricated by separately machining components of the fractionation zone and subsequently mounting those components in a housing.

Manufacturing these devices requires special procedures to obtain satisfactory results. This applies to tolerances, surface conditions, fabrication techniques, materials, and tools/fixturing. For proper functioning of the slot nozzle virtual impactors, it is important to maintain acceptable tolerances on the fractionation zone near the intersection of the acceleration and receiver nozzles. In addition to the tolerances listed in Table 1, the blade surfaces in the fractionation zone should be polished to a surface finish no greater than 0.005 of the acceleration nozzle width.

Any solid engineering material compatible with the fabrication technique can be used to fabricate the devices. Because of the close tolerances, particular attention must be given to warping due to stress relief of hard materials during machining, and problems with machining softer materials that can be difficult to cut with precision. Suitable materials include stainless steel, and aluminum 7075.

Figure 10:
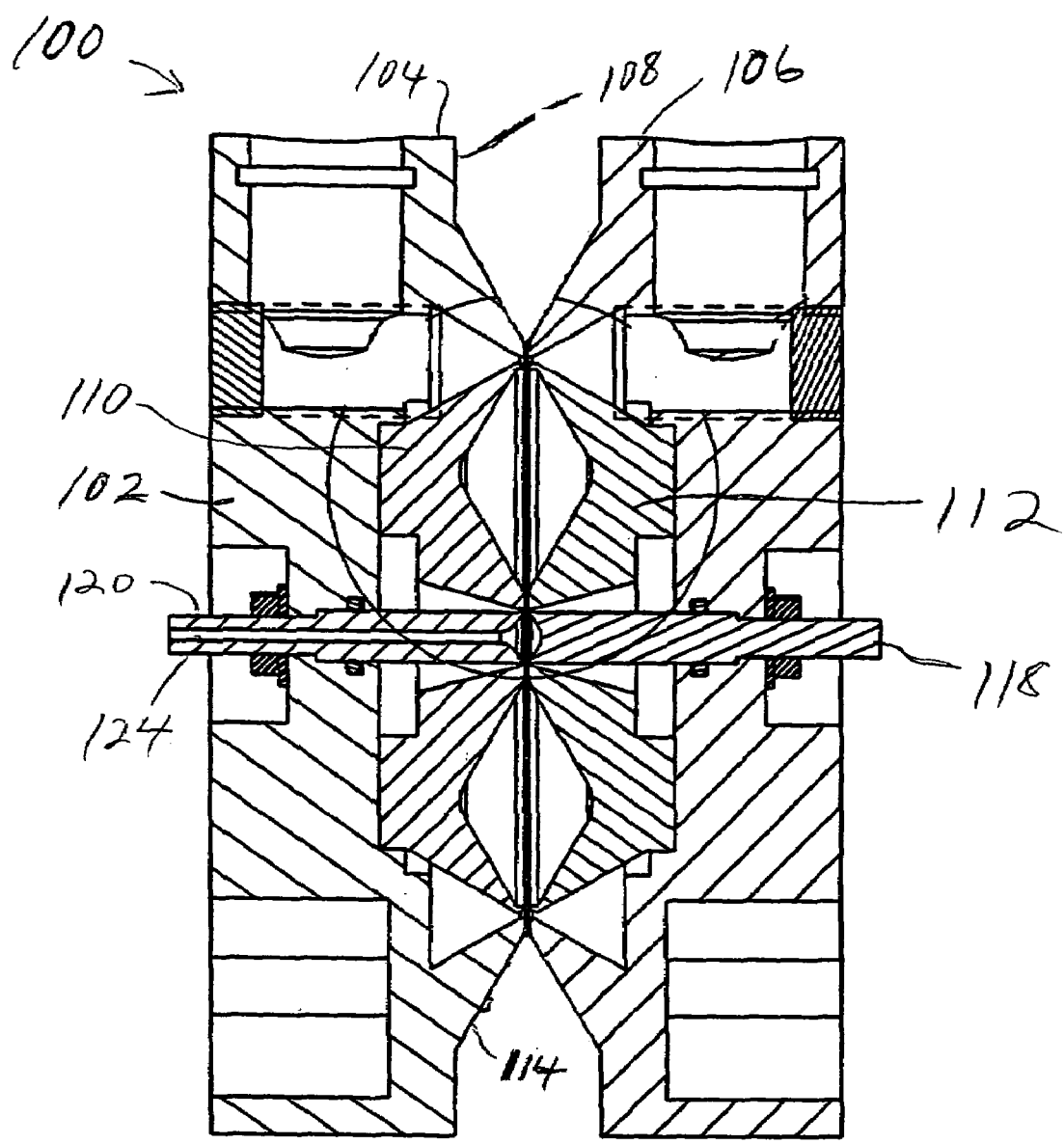
FIG. 10 is a sectional view of a further alternative aerosol particle concentrating device having two concentrating stages.
Figure 11:
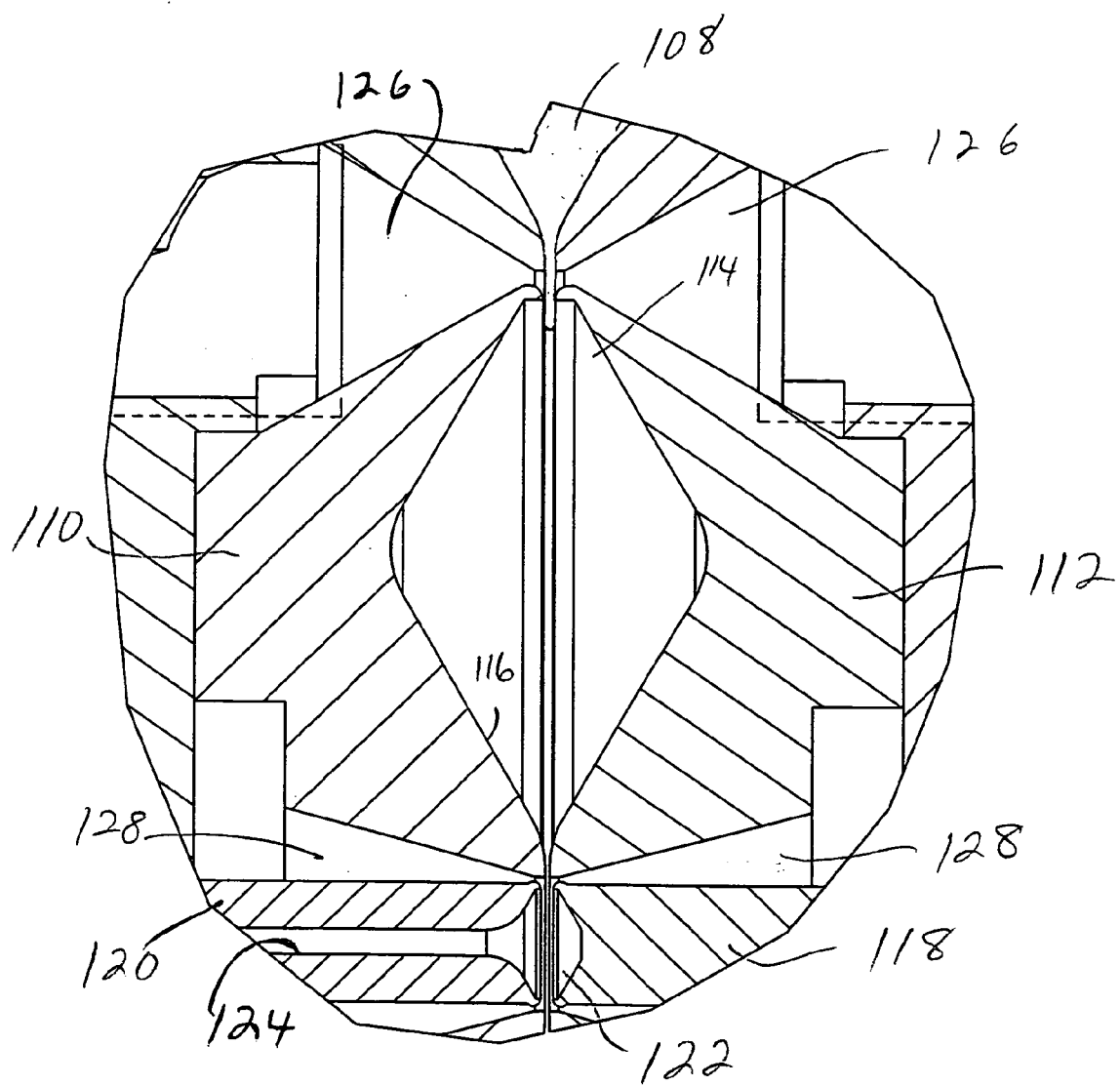
FIG. 11 is an enlarged view showing part of FIG. 10.

FIGS. 10 and 11 are sectional views of a further embodiment circumferential slot virtual impactor in the form of a two-stage device 100. Device 100 includes a cylindrical housing 102 including outer annular nozzle sections 104 and 106 cooperating to form an annular acceleration nozzle 108, and a pair of annular inner nozzle sections 110 and 112 cooperating to form a receiver nozzle 114 spaced apart radially inwardly from nozzle 108. Nozzle sections 110 and 112 also form a second, radially inward acceleration nozzle 116.

The device further includes a pair of opposed central sections 118 and 120 that cooperate to form a second receiver nozzle 122 radially inwardly of acceleration nozzle 116. Central section 118 includes a passage 124 for conducting fluid flows axially from the region of receiver nozzle 122 to the outside of the device.

Device 100 provides two stages of aerosol particle concentration. The aerosol first flows radially inwardly into the housing through the annular, converging slot formed by acceleration nozzle 108. At a fractionation region between nozzles 108 and 114, the primary flow is separated as in previous embodiments, to provide a major or secondary flow leaving the fractionation zone in opposite axial directions through a diverging passage 126, and a minor or tertiary flow into receiver nozzle 114.

The tertiary flow continues to flow radially inward with respect to housing 102, eventually through accelerator nozzle 116. Upon exiting nozzle 116, the tertiary flow is separated into a major fraction that travels outwardly in both axial directions through a passage 128, and a minor fraction that continues radially inward to enter receiver nozzle 122. The minor fraction of the tertiary flow is conducted out of device 100 through passage 124.

It is advantageous to configure both stages to provide a major flow of about 90 percent of the incoming aerosol, and a minor flow of about 10 percent of the incoming aerosol. As a result, the concentration of large particles (i.e. those with aerodynamic diameters above the cutpoint) in the tertiary flow is 10 times the concentration in the primary flow. The concentration in the minor fraction of the tertiary flow is 100 times the concentration in the primary flow. Thus, two-stage device 100 provides a convenient alternative to arranging two single-stage devices in series.

Figure 12:
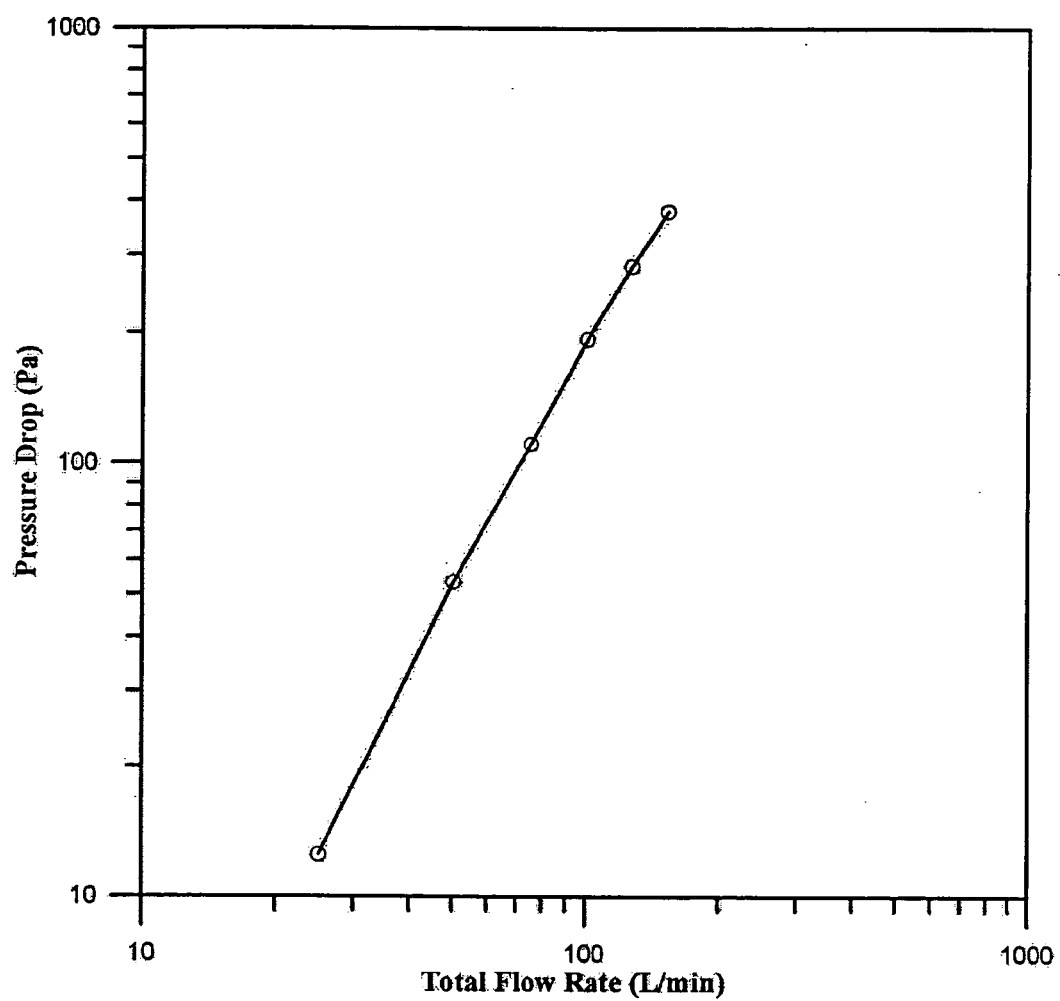
FIG. 12 is a plot of pressure drop as a function of the total aerosol flow rate through a single stage circumferential slot virtual impactor.

The pressure loss incurred in moving air through the virtual impactor is an important consideration for minimizing the size and weight of bioaerosol concentration systems. FIG. 12 is a plot of pressure drop in the major aerosol flow as a function of the flow rate of the primary aerosol flow, with the minor (tertiary) flow rate at ten percent of the primary flow rate. At the nominal design flow rate of 100 L/min, the pressure loss was 190 Pa (0.76 inches of water). The pressure loss coefficient, K, averaged 1.5 for Reynolds numbers from 157 to 367.

Figure 13:
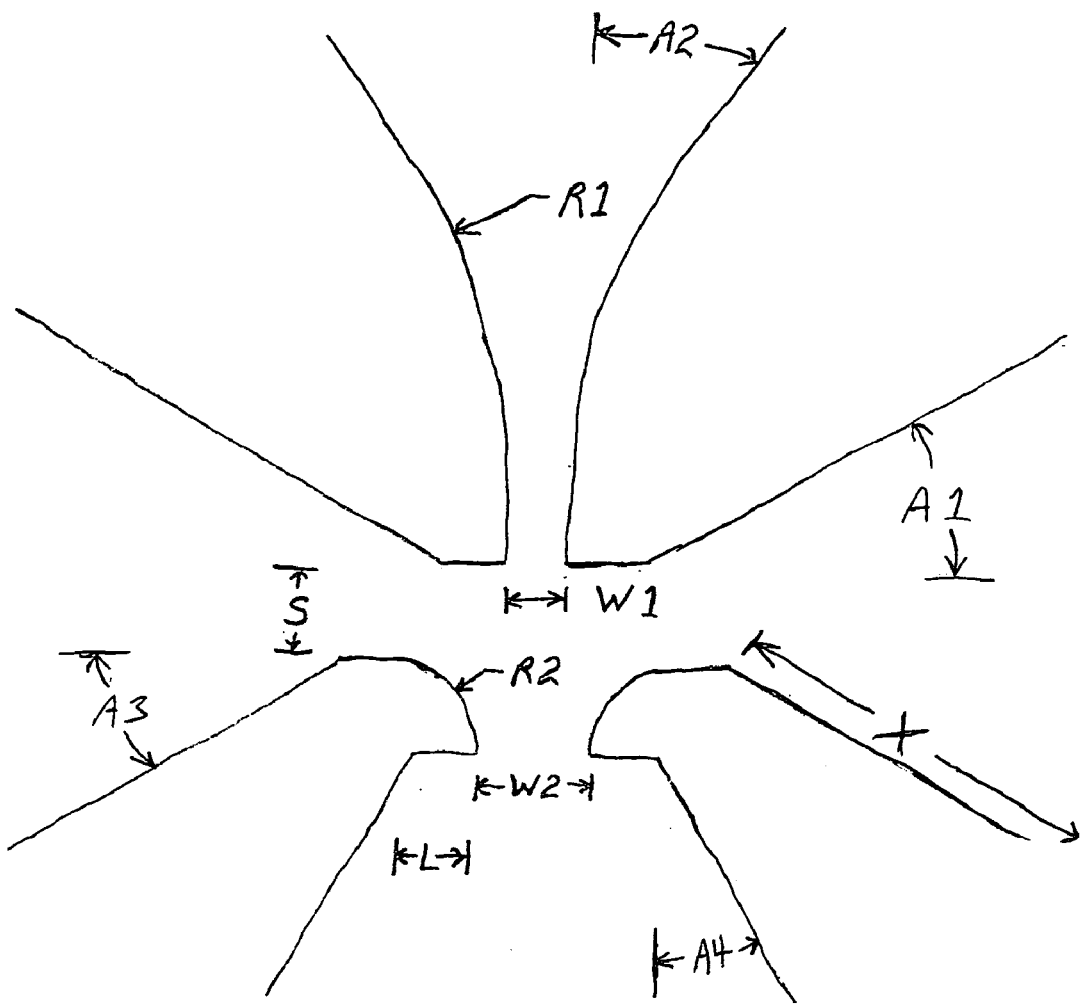
FIG. 13 is a diagram of nozzle interior surface profiles suitable for the device of FIG. 6 and other concentrating devices.

FIG. 13 is a diagram illustrating surface profiles of an acceleration nozzle and a receiver nozzle spaced apart downstream from the accelerator nozzle. It has been found advantageous to size various features with respect to the transverse width of the acceleration nozzle exit aperture, shown as W1 in the figure. As seen in Table 1, other profile parameters are sized with respect to width W1. These features include the width of W2 of the receiver nozzle aperture, the standoff or radial gap S between the accelerator and receiver nozzles, the shoulder L beyond the receiver nozzle aperture, the radius of curvature R1 along the accelerator nozzle interior surface, the radius of curvature R2 at the receiver nozzle aperture, and the angles A1-A4 of the inclined surfaces. Finally, all of the angled surfaces should have a length X at least 50 times width W1.

TABLE 1

Relative Values and Tolerances for Nozzles and Fractionation Zone

| Parameter Description | Value* | Tolerance |
| --- | --- | --- |
| W1: Acceleration Nozzle Width | 1 | ±0.02 |
| W2: Receiver Nozzle Width | 2 | ±0.03 |
| S: Nozzle Stand-off Distance | 1.5 | ±0.06 |
| L1: Receiver Step-out | 0.5 | ±0.12 |
| R1: Acceleration Nozzle Curved Segment Radius | 10 | |
| R2: Receiver Aperture Curvature Radius | 1 | |
| A1: Acceleration Major Flow Expansion Angle | 30° | ±2° |
| A2: Acceleration Nozzle Approach Angle | 30° | ±2° |
| A3: Receiver Major Flow Expansion Angle | 30° | ±2° |
| A4: Receiver Nozzle Expansion Angle | 30° | ±2° |
| X: Expansion Length (all angled surfaces) | 50 | (minimum) |

*all units relative to W1

In one embodiment, the exit aperture width W1 is 0.51 mm (0.02 inches). In another embodiment, the width is 0.25 mm (0.01 inches).

FIGS. 14 and 15 are diagrammatic views of a planar-symmetric (rectangular slot) particle concentration device 130 and an axi-symmetric (truncated conical) particle separation device 132, respectively. Sectional views of devices 130 and 132, taken along lines 134 and 136 respectively, would yield sectional views resembling FIG. 7, with surface profiles substantially the same as those shown in FIG. 13. Thus, devices 130 and 132 incorporate the preferred nozzle geometry, and exhibit the flow smoothing and particle cross-over minimizing advantages discussed above in connection with FIG. 7.

Figure 16:
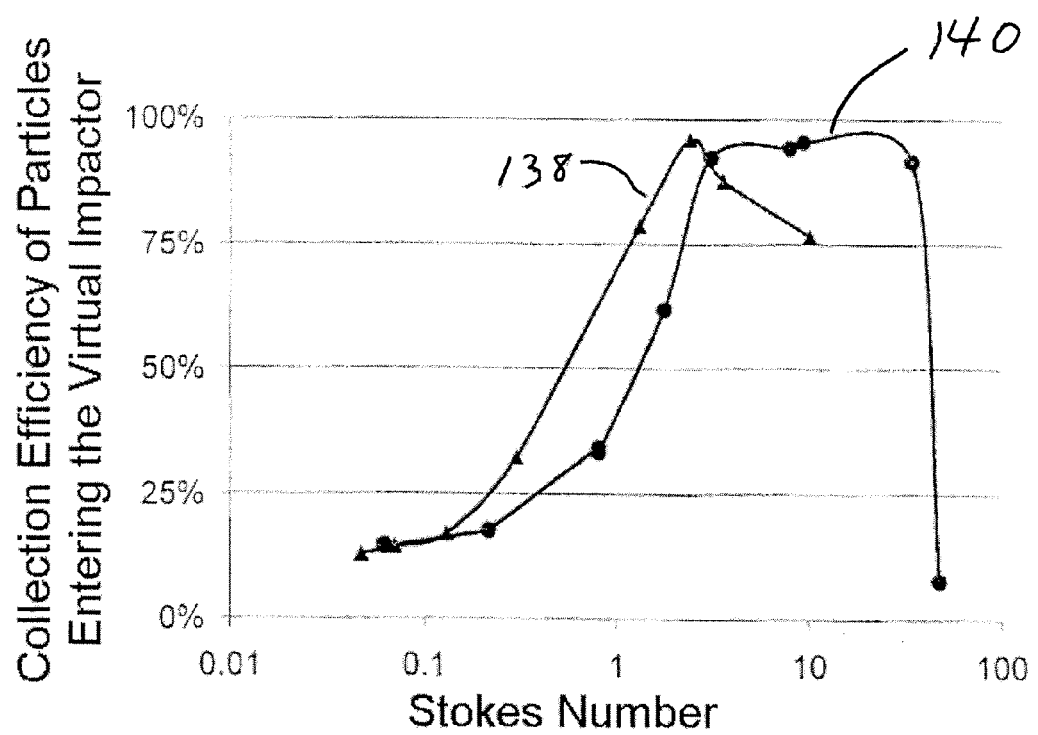
FIG. 16 is a plot of particle collection efficiency as a function of Stokes number for two linear slot virtual impactors, one of which incorporates an arcuate interior surface feature in accordance with the present invention.

FIG. 16 is a plot of collection efficiency as a function of Stokes number for two linear slot virtual impactors. The devices were fabricated and tested for aerosol collection efficiency and examined for wall losses. In one impactor, having an acceleration nozzle with a planar taper to the entry section of the acceleration nozzle (line 138), there is a drop in efficiency with larger-sized particles (Stokes numbers greater than about 2). The improved version (line 140) does not exhibit a drop in efficiency until the Stokes number is about 30. This version has a contoured acceleration nozzle with surface profiles as shown in FIG. 13. The nozzle curvature (R1) reduces the inadvertent deposition of large particles in the fractionation zone. Because proper nozzle geometry is one of the critical parameters influencing virtual impactor performance, the geometry shown in FIG. 13 is preferred. Experimental and computational results have shown the important dimensions to include the receiver nozzle slot width, the radius of curvature of the receiver nozzle inlet section, the angle of convergence of the acceleration nozzle, the radius of curvature of the acceleration nozzle inlet section, the width of the step in the receiver nozzle expansion section and the divergence angle of the receiver nozzle exit section.

FIG. 17A illustrates another alternative embodiment aerosol particle concentrating device 142 similar to previous embodiments, in that the device receives aerosols near its perimeter wall. A housing of the device is polygonal, more particularly hexagonal, rather than circular. A plurality of slots 144 for entry of the aerosol follow the hexagonal perimeter wall 146 of the housing, and thus retain the hexagonal shape. In sections taken perpendicular to the perimeter wall (FIG. 17B), the device resembles device 64 shown in FIGS. 6 and 7, except that the flow directions are rotated ninety degrees. Slots 144 provide an axial inlet. Aerosol enters the device through slots 144 and flows axially through the fractionation zone, where the major (secondary) flow is deflected to the radial direction. The minor flow exits in an axial direction with respect to device 142.

FIG. 18 is a block diagram of an aerosol characterizing system 148 that can employ either two-stage device 100, or a serial pair of the other embodiment devices. An aerosol (e.g. ambient air) is provided through an aerosol sampling inlet 150 to a first virtual impactor stage 152, where the primary aerosol flow is separated into major and minor flows as previously described. The major flow proceeds to a particulate removing filter 154, through a flow meter 156, and then through a valve 159 to a vacuum pump or suction blower 158. A controller 160 receives a flow rate indicating input from the flow meter, and controls valve 159. Returning to particle concentrator stage 152, the minor flow leaves the stage and enters a second virtual impactor stage 162, where the aerosol is again separated into major and minor flows. The major flow proceeds through a filter 164 to a flow meter 166, then through a valve 168 to pump 158. Valve 168 is adjustable through a controller 170 that receives an electrical signal representing the output of flow meter 166.

The minor flow from impactor stage 162 is provided to an aerosol characterizing or receiving device 172. Device 172 can be an optical counter, a particle collector, or a particle characterizing instrument such as a differential mobility analyzer. Device 172 also can be a detection instrument for sensing biological particles. The receiving device output is provided to a microprocessor 174 for recording, analysis and display.

For operation under varying environmental conditions (different levels of ambient temperature and pressure) it is desirable to control the flow rate of the incoming aerosol, the first stage major flow, and the second stage major flow in terms of actual conditions, i.e. to set volumetric flow rates based on the ambient pressure and temperature.

Thus in accordance with the present invention, a particle concentration device draws aerosols inward through a circumferential slot to achieve a favorable combination of a narrow slot, a high ratio of slot length to slot width, and a compact overall design that achieves satisfactory flow rates at low power consumption. The slot has angular inclined opposed interior surfaces that converge inwardly to accelerate the incoming aerosol. Further, the interior surfaces incorporate a convex curvature to smooth the aerosol flow and reduce episodes of large-particle deposition onto the acceleration nozzle exit aperture. The devices can be employed serially to multiply the particle concentration effect. Alternatively, a single embodiment can incorporate several particle concentration stages.

What is claimed is:

1. A particle concentrating device for separating a primary aerosol flow into secondary and tertiary aerosol flows with different particulate concentrations, including:

a housing having a perimeter wall;

the housing including a housing structure defining a first fluid passage running lengthwise along the perimeter wall, open to an exterior of the housing, and extending inward from the housing wall to a first-passage exit to accommodate a primary flow of an aerosol in an inward first direction with respect to the housing, wherein the aerosol comprises a gaseous medium and particles suspended in the medium and the particles comprise first particles having aerodynamic diameters above a selected threshold and second particles having aerodynamic diameters below the selected threshold;

the housing structure further defining a second fluid passage downstream of the first fluid passage, to accommodate fluid flow away from the first-passage exit in a second direction different from the first direction;

the housing structure further defining a third fluid passage disposed inwardly of the first fluid passage, to accommodate fluid flow away from the first-passage exit in the first direction;

a first fluid-drawing component in fluid communication with the second fluid passage, adapted to draw a first portion of the primary flow toward and into the second fluid passage and thereby deflect the gaseous medium and second particles of said first portion while the first particles of said first portion tend to continue moving in the first direction due to particle momentum, thus to provide a secondary flow of the aerosol through the second fluid passage; and a second fluid-drawing component in fluid communication with the third passage, adapted to draw a second portion of the primary flow inward toward and into the third fluid passage, thus to provide a tertiary flow of the aerosol through the third fluid passage, the tertiary flow comprising the gaseous medium and particles of said second portion merged with first particles of said first portion.

2. The device of claim 1 wherein:

a part of the housing structure defining the first fluid passage includes opposed interior surfaces oriented to define a convergence in the first direction from a relatively wide first-passage entrance to the first-passage exit.

3. The device of claim 2 wherein:

the first-passage exit has a substantially uniform width.

4. The device of claim 3 wherein:

the opposed interior surfaces incorporate respective first and second arcuate segments, each arcuate segment having a convex profile with a radius of curvature in the range of 5-15 times the width of the first-passage exit.

5. The device of claim 4 wherein:

the opposed interior surfaces further incorporate respective first and second exit region surface segments downstream of the arcuate segments and having linear profiles extending in the first direction.

6. The device of claim 2 wherein:

a part of the housing defining the third fluid passage includes opposed inside surfaces oriented to provide a divergence of the third fluid passage in the first direction.

7. The device of claim 2 wherein:

a part of the housing defining the second fluid passage includes opposed inside surfaces oriented to provide a divergence of the second fluid passage in the second direction away from the first-passage exit.

8. The device of claim 1 wherein:

the second direction is substantially perpendicular to the first direction.

9. The device of claim 1 wherein:

the housing is generally disk shaped, whereby the perimeter wall has a circular profile, the first direction is radially inward, and the second direction is axial with respect to the housing.

10. The device of claim 1 wherein:

the first fluid-drawing component and the second fluid-drawing component together comprise at least one vacuum pump.

11. The device of claim 10 further including:

a first valve in fluid communication with the second fluid passage and the at least one vacuum pump, a second valve in fluid communication with the third fluid passage and the at least one vacuum pump, and a control component operably associated with the first and second valves to control first and second fluid flow rates of the secondary and tertiary flows through the first and second valves, respectively.

12. The device of claim 11 wherein:

the first and second valves are controlled to provide the first flow rate at about ninety percent of a primary flow rate of the primary flow, and the second flow rate at about ten percent of the primary flow rate.

13. The device of claim 1 wherein:

the housing structure further defines a fourth fluid passage disposed inwardly of the third fluid passage adapted to receive and accommodate the tertiary flow and having a fourth-passage exit, a fifth fluid passage downstream of the fourth fluid passage to accommodate fluid flow away from the fourth-passage exit in a third direction different from the first direction, and a sixth fluid passage disposed inwardly of the fourth fluid passage to accommodate fluid flow away from the fourth-passage exit in the first direction;

a third fluid-drawing component in fluid communication with the fifth fluid passage, adapted to draw a first part of the tertiary flow toward and into the fifth fluid passage and thereby deflect the gaseous medium and second particles of said first part while the first particles of said first part tend to continue moving in the first direction due to particle momentum, thus to provide a first fractional flow of the aerosol through the fifth fluid passage; and a fourth fluid-drawing component in fluid communication with the sixth passage, adapted to draw a second part of a tertiary flow inward toward and into the sixth fluid passage, thus to provide a second fractional flow of the aerosol through the sixth fluid passage, the second fractional flow comprising the gaseous medium and particles of said second part merged with first particles of said first part.

14. The device of claim 13 wherein:
the third direction substantially coincides with the first direction.

15. The device of claim 14 wherein:
the perimeter wall has a circular profile, the first direction is radially inward, and the second and third directions are axial with respect to the housing.

16. The device of claim 1 further including:
an aerosol characterizing apparatus fluid coupled to the housing to receive at least a portion of the tertiary flow.

17. The device of claim 16 wherein:
the aerosol characterizing apparatus includes at least one component selected from the group consisting of: particle counting components, particle collecting components, and biological particle detecting components.

18. A process for separating an aerosol into fractions with different particulate concentrations, including:
causing an aerosol to enter an enclosure through an entrance along a perimeter wall of the enclosure and to flow inside the enclosure in a first direction toward an interior region of the enclosure, wherein the aerosol comprises a gaseous medium and particles suspended in the medium, and the particles comprise first particles having aerodynamic diameters above a selected threshold and second particles having aerodynamic diameters below the selected threshold;

at a fractionation region in the enclosure, causing the gaseous medium and second particles of a first portion of the aerosol to flow in a second direction different from the first direction while the first particles of said first portion continue to move in the first direction due to particle momentum, thus to provide a first fractional flow of the aerosol including the gaseous medium and second particles of said first portion;

simultaneously at the fractionation region, causing a second portion of the aerosol to continue flowing in the first direction, thus to provide a second fractional flow of the aerosol comprising the gaseous medium and particles of said second portion in combination with the first particles of said first portion.

19. The process of claim 18 wherein:
causing the aerosol to enter the enclosure comprises accelerating the aerosol.

20. The process of claim 18 wherein:
causing the aerosol to enter the enclosure comprises causing the aerosol to move through a circumferential slot in the perimeter wall and radially inward in the first direction with respect to the enclosure.

21. The process of claim 20 wherein:
causing the gaseous medium and second particles of said first portion to flow in the second direction comprises generating a flow in an axial direction with respect to the enclosure.

22. The process of claim 18 wherein:
causing the gaseous medium and second particles of said first portion to flow in the second direction, and causing the second portion of the aerosol to continue flowing in the first direction, comprise using a vacuum to draw the aerosol.

23. The process of claim 22 further including:
controlling vacuum levels applied to the first fractional flow and second fractional flow to control respective first and second flow rates of the fractional flows with respect to one another.

24. The process of claim 23 wherein:
controlling the first and second flow rates comprises maintaining the first flow rate at about nine times the second flow rate.

25. The process of claim 18 further including:
at a selected region downstream of the fractionation region, deflecting the gaseous medium and second particles of a first part of the second fractional flow to a third direction different from the first direction while the first particles of said first part tend to continue moving in the first direction due to particle momentum, thus to provide a third fractional flow of the aerosol including the gaseous medium and second particles of said first part; and simultaneously at the selected region, causing a second part of the second fractional flow to continue flowing in the first direction, thus to provide a fourth fractional flow of the aerosol comprising the gaseous medium and particles of said second part in combination with first particles of said first part.

26. The process of claim 18 further including:
characterizing at least a portion of the aerosol of the second fractional flow.

27. The process of claim 26 wherein:
characterizing at least a portion of the aerosol comprises a step selected from the group consisting of: counting particles, collecting particles, and detecting biological particles.

28. The process of claim 18 wherein:
causing the gaseous medium and second particles of said first portion to flow in a second direction comprises causing said gaseous medium and second particles to flow perpendicular to the first direction.

29. An aerosol particle concentrating device including:
an acceleration nozzle including a nozzle entrance, a nozzle exit including an exit aperture, and a nozzle wall having an interior surface running from the entrance to the exit and defining a first fluid passage for accommodating an aerosol flow through the acceleration nozzle in a first longitudinal direction from the entrance to the exit, wherein the exit aperture has a major transverse dimension and a minor transverse dimension;

structure defining a second fluid passage downstream of the first fluid passage to accommodate fluid flow away from the nozzle exit in a second direction different from the first longitudinal direction, and a third fluid passage longitudinally downstream from the first fluid passage to accommodate fluid flow away from the nozzle exit in the first longitudinal direction; and a fluid-drawing component in communication with the second and third fluid passages for drawing first and second fractions of the aerosol flow into and through the second and third fluid passages, respectively, while at least some of the particles of the first fraction separate from the first fraction and enter the third fluid passage with the second fraction due to particle momentum;

wherein the interior surface, at least in and along longitudinal planes taken through the acceleration nozzle in the direction of the minor transverse dimension, forms pairs of opposed surface profiles on opposite sides of a longitudinal axis through the acceleration nozzle;

wherein the profiles incorporate respective arcuate segments between the entrance and the exit aperture, each arcuate segment being convex in a direction toward the longitudinal axis, and wherein the opposed arcuate segments converge in said first longitudinal direction to diminish the transverse distance between the opposed surface profiles.

30. The device of claim 29 wherein:

said surface profiles further incorporate linear segments between the arcuate segments and the nozzle entrance, inclined relative to the longitudinal axis.

31. The device of claim 29 wherein:

said surface profiles along the exit aperture are parallel to the longitudinal axis.

32. The device of claim 31 wherein:

the surface profiles along the exit aperture form tangents to their respective arcuate segments.

33. The device of claim 29 wherein:

each of the arcuate segments has a radius of curvature at least five times the minor transverse dimension of the exit aperture.

34. The device of claim 29 wherein:

the acceleration nozzle is annular whereby the nozzle entrance is circumferential, the first longitudinal direction is radial with respect to the nozzle, and the minor transverse direction is axial relative to the nozzle.

35. The device of claim 29 wherein:

the acceleration nozzle is elongate and linear, the exit aperture is rectangular and has a transverse length and width, and the minor transverse dimension comprises the width.

36. The device of claim 29 wherein:

the exit aperture is circular and concentric on the longitudinal axis, whereby the major transverse dimension and the minor transverse dimension constitute diameters of the exit aperture and are substantially equal.

37. The device of claim 29 wherein:

the structure providing the third fluid passage comprises a receiver nozzle spaced apart from the acceleration nozzle in the first longitudinal direction and having a nozzle interior that diverges in the first longitudinal direction.

38. The device of claim 37 wherein:

the second fluid passage diverges in directions transversely away from the longitudinal axis.

* * * * *

UNITED STATES PATENT AND TRADEMARK OFFICE
CERTIFICATE OF CORRECTION

PATENT NO. : 7,261,007 B2  Page 1 of 1
APPLICATION NO. : 10/995745
DATED : August 28, 2007
INVENTOR(S) : Haglund et al.

It is certified that error appears in the above-identified patent and that said Letters Patent is hereby corrected as shown below:

Column 7, Line 24:
After "accordance" insert --with--.

Column 8, Line 49:
"60" should be bolded.

Signed and Sealed this

Eighth Day of July, 2008

JON W. DUDAS
*Director of the United States Patent and Trademark Office*